US006162450A

United States Patent [19]
Ptchelintsev et al.

[11] Patent Number: 6,162,450
[45] Date of Patent: *Dec. 19, 2000

[54] USES OF ASCORBYL-PHOSPHORYL-CHOLESTEROL AND COMPOSITIONS FOR PRACTICING SAME

[75] Inventors: Dmitri Ptchelintsev, Mahwah; John A. Duffy, West Milford; Robert Kalafsky, Ogdensburg; Harold E. Pahlck, Waldwick, all of N.J.

[73] Assignee: Avon Products, Inc., New York, N.Y.

[*] Notice: This patent is subject to a terminal disclaimer.

[21] Appl. No.: 09/189,368

[22] Filed: Nov. 9, 1998

Related U.S. Application Data

[63] Continuation-in-part of application No. 09/126,191, Jul. 30, 1998, Pat. No. 5,922,335, which is a continuation-in-part of application No. 08/853,271, May 9, 1997, Pat. No. 5,951,990, which is a continuation-in-part of application No. 08/837,282, Apr. 11, 1997, Pat. No. 5,866,147, which is a continuation of application No. 08/440,765, May 15, 1995, abandoned.

[51] Int. Cl.$^7$ .............. A61K 7/00; A61K 7/02; A61K 7/025; A61K 7/04; A61K 7/047

[52] U.S. Cl. .............. 424/401; 424/59; 424/60; 424/61; 424/62; 424/63; 424/64; 514/169; 514/171; 514/474; 514/725; 514/844; 514/845; 514/846; 514/847; 514/937; 514/944; 514/945

[58] Field of Search .................. 424/401, 450, 424/59, 60, 61, 63, 64; 514/169, 171, 474, 725, 844–847, 944, 945, 937

[56] References Cited

U.S. PATENT DOCUMENTS

| | | |
|---|---|---|
| 3,151,127 | 9/1964 | Spanel . |
| 4,254,105 | 3/1981 | Fukuda . |
| 4,564,686 | 1/1986 | Ogata . |
| 4,919,921 | 4/1990 | Hatae . |
| 4,939,128 | 7/1990 | Kato ................... 514/82 |
| 4,956,355 | 9/1990 | Prendergast . |
| 4,960,764 | 10/1990 | Figueroa, Jr. et al. . |
| 5,053,222 | 10/1991 | Takasu et al. . |
| 5,061,733 | 10/1991 | Bryce et al. . |
| 5,075,333 | 12/1991 | Bryce et al. . |
| 5,110,950 | 5/1992 | Seib et al. . |
| 5,122,536 | 6/1992 | Perricone . |
| 5,229,378 | 7/1993 | Ogata et al. . |
| 5,306,713 | 4/1994 | Suetsugu et al. . |
| 5,308,621 | 5/1994 | Taylor et al. . |
| 5,318,987 | 6/1994 | Weithmann et al. . |
| 5,336,485 | 8/1994 | Fariss . |
| 5,474,991 | 12/1995 | Ogata et al. . |
| 5,474,992 | 12/1995 | Ogata et al. . |
| 5,478,815 | 12/1995 | Ogata et al. . |
| 5,480,909 | 1/1996 | Sanko . |
| 5,508,275 | 4/1996 | Weithmann et al. . |
| 5,516,793 | 5/1996 | Duffy . |
| 5,556,842 | 9/1996 | Shimizu et al. . |
| 5,574,063 | 11/1996 | Perricone . |
| 5,607,968 | 3/1997 | Ptchelintsev . |
| 5,621,008 | 4/1997 | Ptchelintsev . |
| 5,660,976 | 8/1997 | Ishimura et al. . |
| 5,683,704 | 11/1997 | Ohba et al. . |
| 5,703,122 | 12/1997 | Duffy . |
| 5,866,147 | 2/1999 | Ptchelintsev ............... 424/401 |
| 5,922,335 | 7/1999 | Ptchelintsev ............... 424/401 |
| 5,951,990 | 9/1999 | Ptchelintsev ............... 424/401 |

FOREIGN PATENT DOCUMENTS

| | | |
|---|---|---|
| 0 236 120 A2 | 9/1987 | European Pat. Off. . |
| 0 503 582 A1 | 9/1992 | European Pat. Off. . |
| 92104149 | 9/1992 | European Pat. Off. . |

OTHER PUBLICATIONS

Menon, et al., Structural Basis for the Barrier Abnormality Following Inhibition of HMG CoA Reductose in Murine Epidermis, J. Invest. Dermol., vol. 98, pp. 209–219 (1992).

Hans Steinhart, et al, Pro–and Antioxidative Effect of Ascobic Acid on L–Tryptophan in the System FE3 +/Ascorbic Acid/O2, J. Agric. Food Chem., vol. 41, pp. 2275–2277 (1993).

Sakamoto, et al., Measurement Method of Efficacy of Anti–dandruff Cosmetics and Development of the New Active Commercial Product, IFSCC, Yokohama, vol. B206, pp. 823–864 (1993).

Juva, Anal. Biochem., vol. 15, pp. 77–83 (1966).

Sagarin, Cosmetics, Science and Technology, 2nd Ed. vol. 1, pp. 32–43 (1972).

J. Cosmet, Cham., vol. 29, p. 185 (1978).

Szoka et al., Proc. Nat. Acad. Sciences, vol. 75, pp. 4194–4198 (1978).

Evans, Chromatographia, vol. 13, pp. 5–10 (1980).

Booth, Biochem, Biophys. Acta, vol. 675, pp. 117–122 (1981).

Mezei, J. Pharmaceut. Pharmacol., vol. 34, pp. 473–474 (1982).

Mezei, Topics in Pharmaceutical Sciences, Breimer et al. Eds., pp. 345–358, Elsevier Science Publishers BV, New York (1985).

Rainsford, Antiflammatory and Anti–Rheumatic Drugs, vol. I–III, CRC Press, Boca Raton, Florida (1985).

McCutcheon, Detergents and Emulsifiers, North American Edition, pp. 317–324 (1986).

Diploses et al., J. Soc. Cosmetics Chemists, vol. 43, pp. 93–100 (1992).

*Primary Examiner*—Gollamudi S. Kishore
*Attorney, Agent, or Firm*—Ohlandt, Greeley, Ruggiero & Perle, L.L.P.

[57] ABSTRACT

The present invention relates to the use of 3'-(L-ascorbyl-2-o-phosphoryl)-cholesterol, 3'-(L-ascorbyl-3-o-phosphoryl)-cholesterol, and their derivatives ("APC compounds"). More specifically, the present invention relates to use of APC compounds to improve the appearance and health of skin, hair, lips and nails. The present invention also relates to methods of topically administering APC compounds to cleanse skin and remove make-up, moisturize skin, enhance the shine and wear of nail coating compositions, and to improve compositions having pigments and/or iron oxides.

25 Claims, No Drawings

USES OF ASCORBYL-PHOSPHORYL-CHOLESTEROL AND COMPOSITIONS FOR PRACTICING SAME

RELATED APPLICATIONS

This application is a continuation-in-part of U.S. patent application Ser. No. 09/126,191, filed Jul. 30, 1998 now U.S. Pat. No. 5,922,335, which is a continuation-in-part of U.S. patent application Ser. No. 08/853,271, filed May 9, 1997 now U.S. Pat. No. 5,951,990, which is a a continuation-in-part of U.S. patent application Ser. No. 08/837,282, filed Apr. 11, 1997 now U.S. Pat. No. 5,866,147, which is a continuation of Ser. No. 08/440,765 filed May 15, 1995 which is abandoned.

BACKGROUND OF THE INVENTION

1. Field of the Invention

The present invention relates to novel topical compositions. More particularly, the present invention is directed to topical compositions that have 3'-(L-ascorbyl-2-o-phosphoryl)-cholesterol, 3'-(L-ascorbyl-3-o-phosphoryl)-cholesterol, and their derivatives (hereinafter collectively referred "APC compound" or "APC compounds"). The present invention also relates to novel uses of topical compositions having APC compounds to enhance the appearance and health of skin, lips and nails. The present invention also relates to novel compositions that have APC compounds in an amount sufficient to synergistically enhance the activity and benefits of typical cosmetic adjuvants, such as sunscreens and pigments. The present invention further relates to novel methods of topically administering compositions having APC compounds, such as with a lipstick or a dermal patch.

2. Description of Related Art

U.S. Pat. No. 4,939,128 to Kato et al. is directed to the use of phosphoric acid esters of ascorbic acid for the treatment of systemic diseases, and not for cosmetics, topical dermatological or skin uses. This patent provides that certain phosphoric acid esters of ascorbic acid display improved oxygen-scavenging properties. However, the specific mention of a cholestenyl group suggests that conjugates of L-ascorbic acid and cholesterol were neither practical nor desired. The Kato et al. patents fail to disclose phosphoric acid diesters of ascorbic acid and cholesterol, and the synergistic results that may be obtained in topical compositions through the incorporation of effective amounts of APC compounds.

U.S. Pat. No. 5,607,968 to Ptchelintsev provides a method of making ascorbic acid-phosphoryl derivatives that incorporate straight chain ($C_2$ to $C_{18}$) alkyl groups.

Heretofore, consumers desired cosmetic compositions that have been synergistically improved by incorporating APC compounds therein. Consumers also desired additional methods of improving the health and appearance of their skin, nails and lips using such APC compounds.

BRIEF SUMMARY OF THE INVENTION

It is an object of the present invention to provide a novel method of removing cosmetics, such as makeup, that efficiently cleans the skin and also improves the general health and appearance of the skin.

It is also an object of the present invention to provide a novel method for cleansing skin, hair and nails.

It is another object of the present invention to provide a method of moisturizing skin.

It is still another object of the present invention to provide a method of improving the health and appearance of lips, skin and nails.

It is yet another object of the present invention to provide a method of providing the benefits of ascorbic acid in a cosmetic composition having iron oxides without significantly increasing the oxidation of the cosmetic composition.

It is a further object of the present invention to provide improved cosmetic compositions having a pigment that exhibits improved dispersion of the pigment.

It is still further an object of the present invention to provide a nail coating that exhibits enhanced shine/gloss once cured.

It is yet further an object of the present invention to provide a nail enamel/polish that exhibits increased resistance to chipping, peeling and abrasion of the cured nail coating.

It is still another object of the present invention to provide a topical cosmetic composition having a synergistic combination of at least one APC compound and a sunscreen.

It is yet another object of the present invention to provide a novel method of topically administering APC compounds to localized areas.

The present invention, in brief summary, is topical compositions having APC compounds, and methods of administering these topical compositions to improve the condition of skin, hair and nails as well as their appearance.

DETAILED DESCRIPTION OF THE INVENTION

Although the individual benefits of ascorbic acid and cholesterol are known, mechanical mixing of L-ascorbic acid and cholesterol results in an unstable product due to the instability of L-ascorbic acid. Free L-ascorbic acid in topical preparations demonstrates poor stability and tends to break down due to oxidative and/or non-oxidative degradation. The degraded ascorbic acid loses activity and the resultant product loses aesthetic appeal since it exhibits a cosmetically undesired brown color.

However, APC compounds provide advantages not available from simple admixtures of ascorbic acid and cholesterol without the disadvantages associated with ascorbic acid. In the APC compounds, the conjugated ascorbic acid becomes resistant to degradation. This benefits the consumer by providing a more stable, more effective, and more aesthetically pleasing product.

In addition to the increased stability demonstrated by topical compositions having APC compounds rather than ascorbic acid, APC compounds also provide other advantages. For example, APC compounds are better absorbed through the skin since the cholesteryl group serves as a carrier moiety and facilitates delivery of polar ascorbic acid through the non-polar outermost protective layer of skin (i.e., the stratum corneum) and increases the bioavailability of the ascorbic acid in the topical composition.

Although the L-ascorbic acid is covalently bound to the cholesterol by a phosphoryl or phosphate group, natural enzymes, such as phosphatases that are present in the skin, gradually cleave the phosphoryl or phosphate linkage between cholesterol and ascorbic acid, resulting in sustained release of free L-ascorbic acid and cholesterol into the stratum corneum. The released cholesterol is a natural substrate for skin and supplements that otherwise produced by the body. Topically applied cholesterol improves elasticity, tone and resistance to drying.

Co-pending U.S. applications Ser/ Nos. 08/837,282, 08/853,271, and 09/126,191, the entire disclosures of which are incorporated herein by reference, provide stable topical compositions comprising the APC compounds, namely 3'-(L-ascorbyl-2-o-phosphoryl)-cholesterol, 3'-(L-ascorbyl-3-o-phosphoryl)-cholesterol, and their derivatives. Such suitable stable topical compositions comprising APC compounds include from about 0.05 wt % to about 50 wt %, preferably from about 0.1 wt % to about 20 wt %, and more preferably from about 1 wt % to about 10 wt %. APC compounds in topical compositions provide beneficial effects of decreasing abnormal elastin production, decreasing free-radical formation, and increasing keratinocyte triglyceride synthesis. APC compounds provide beneficial effects of both L-ascorbic acid and cholesterol on skin by providing increased collagen production and skin-lightening associated with ascorbic acid and by improving elasticity, resistance, tone and moisture retention of the skin associated with cholesterol.

APC compounds include 3'-(L-ascorbyl-2-o-phosphoryl)-cholesterol, 3'-(L-ascorbyl-3-o-phosphoryl)-cholesterol, functional or structural isomers thereof and salts thereof ("APC compounds"). The exemplary compounds include functional or structural isomers of 3'-(L-ascorbyl-2-o-phosphoryl)-cholesterol (Formula I) such as 3'-(L-ascorbyl-3-o-phosphoryl)-cholesterol (Formula II). Both formulas are illustrated below.

cosmetics, dirt and oil from the skin, hair and nails. In addition, since APC compounds are useful in topical preparations or compositions for improving signs of dermatological aging, such as wrinkling in the eye areas or "crows feet," or fine wrinkles around the mouth area, the use of APC compounds in cosmetic cleansing or make-up remover compositions, especially on the sensitive skin areas around the eyes and mouth, will provide consumers with a single product having the dual benefits of cleansing and improving dermatological health. The cosmetic cleansing compositions may be in the form of a cream, a lotion, an emulsion, a gel, an ointment, a foam, a spray or a mousse. However, it is preferred that the cosmetic cleansing composition is a cream, a lotion or an emulsion.

A topical composition having APC compounds may be a moisturizer to alleviate dry skin. Although applicant does not wish to be bound to any theory, it is believed that APC compounds provide moisturizing benefits in at least one of two ways. When the cholesteryl group is cleaved from the APC compound, the cholesterol moiety is a natural substrate for the skin and is associated with increased moisture retention and increased suppleness exhibited by skin. Also, APC compounds have been found to increase keratinocyte triglyceride synthesis. Increased triglyceride synthesis is believed to enhance moisture retention and suppleness exhibited by skin. Most likely, both of the aforementioned factors contribute to the moisturizing effects.

Moisturizing topical compositions of the present invention have from about 0.1 wt % to about 20 wt % of the APC

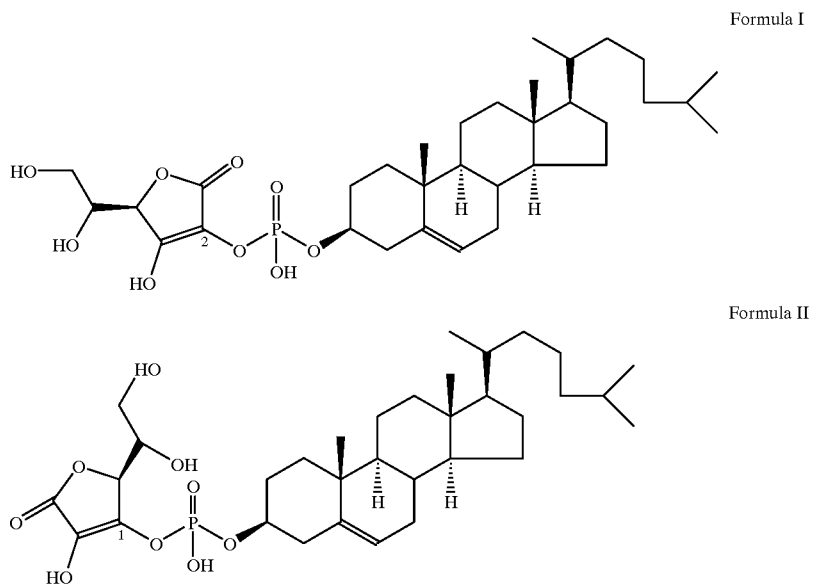

Formula I

Formula II

The preferred APC compound is 3'-(L-ascorbyl-2-o-phosphoryl)cholesterol, salts thereof and derivatives thereof.

Exemplary salts of the APC compound include ammonium, calcium, lithium, potassium or sodium salts. Salts of the APC compounds can be incorporated, either individually or with the L-ascorbic derivative, into a topical vehicle. A salt with an organic amine, such as ethanolamine, may also be used in combination with the APC compound.

Although some benefits of APC compounds have been disclosed, the synergistic combinations of APC compounds with known cosmetic ingredients disclosed herein are novel.

The presence of both a hydrophilic portion (the ascorbyl group) and a lipophilic portion (the cholesteryl group) is believed to provide surfactant activity that aids in removal of compound. More preferably, moisturizing topical compositions of the present invention have from about 1 wt % to about 10 wt % of the APC compound. Copending U.S. patent application Ser. Nos. 08/837,282 and 08/853,271 provide examples of lotions, emulsions, and microemulsions useful for practicing the method of moisturizing skin by topically applying compositions having APC compounds.

A preferred example of a topical composition of the present invention for use as a moisturizer has from about 2 wt % to about 5 wt %, more preferably about 2.5 wt %, of the APC compound in a suitable topical vehicle. If the moisturizer is to be applied for wear during daytime hours, the moisturizer preferably has from about 0.1 wt % to about 25 wt % of a sunscreen. In addition, the vehicle may contain additional conventional additives and adjuvents, which are discussed below.

As has been disclosed, topical application of APC compounds improves collagen synthesis. The topical application of APC compounds directly to the lip is expected to increase collagen synthesis and, thus, improve the appearance of the lips. The increase in collagen synthesis is also expected to create fuller lips. Although APC compounds may be, or may be incorporated into, lip cosmetics, such as lipsticks, lip balms and pomades, it is preferred that the APC compound is, or is incorporated into, a lipstick composition. Lipsticks provide consumers with easy application precisely on the lip area. Lip cosmetics of the present invention may be pigmented or non-pigmented. However, as will be discussed below, the use of APC compounds in pigmented cosmetics, such as lip cosmetics, provides a novel method of improving the appearance and performance of pigmented cosmetics.

Cosmetic compositions often have pigments incorporated therein. An example of such pigments are iron oxides. Previously, the incorporation of ascorbic acid into a topical compositions having iron oxides usually resulted in an increase in oxidation. (The term "iron oxides" as used herein describes one or more iron oxides.) The increased oxidation, in turn, results in the cosmetic composition becoming discolored, less efficacious and, accordingly, less attractive to consumers. It has been found that when an APC compound is incorporated into cosmetic compositions containing iron oxides, there is unexpectedly little or no increase in the oxidation typically associated with ascorbic acid. Thus, incorporating the APC compound into a cosmetic composition having iron oxides is a novel method for improving the appearance of the skin while providing the advantages of both ascorbic acid and iron oxides.

An example of such a topical composition may have from about 0.2 wt % to about 20 wt % of iron oxides in addition to the APC compound. One preferred example of such a topical composition has from about 5 wt % to about 7 wt % of iron oxides and about 1 wt % of the APC compound in a suitable vehicle. In the preferred example, the iron oxides are selected from the group consisting of iron oxide red 2259-preserved, iron oxides (yellow), iron oxides (black), and mixtures thereof.

The addition of one or more APC compounds to compositions enhances surface dispersion of pigments. As was discussed above, APC compounds have both hydrophilic and lipophilic groups. As a result APC compounds assist in decreasing surface tension that allows pigments to "wet out" or disperse effectively. When used with a pigment component, the APC compounds act as a pigment wetter, binder and disperser of the pigment.

It has been discovered that not only do APC compounds enhance the spreadability of topical pigmented compositions, but also that the topical pigmented compositions of the present invention exhibit a self-leveling effect. This self-leveling effect results in greater uniformity with regard to the thickness of the layer of the applied pigmented topical composition. While this self-leveling effect is beneficial to all pigmented compositions, it is particularly useful in topical pigmented compositions such as lipsticks, foundations, and nail enamels/polishes. Thus, topical compositions having APC compounds as a pigment additive are expected to exhibit superior coverage upon application. In addition, when the topical pigmented composition of the present invention is a cosmetic such as foundation, the addition of the APC compounds is expected to provide a superior feel upon application to the skin.

This dispersion assisting property of APC compounds is also believed to improve the coating characteristics of nail compositions. In addition, the use of APC compounds as, or in, nail coating compositions, such as nail enamels or polishes, is expected to enhance the gloss/shine exhibited once the nail coating composition has cured, and to also increase resistance to wear due to chipping, peeling and abrasion. The benefits of improving the health and appearance of the nails is not limited to the incorporation of APC compounds into nail coating compositions, such as nail enamels discussed above. In fact, it is believed that the APC compounds can themselves be the nail coating composition. In copending U.S. application Ser. No. 08/853,271, it was disclosed that APC compounds are useful for treating disorders associated with the nails and cuticles. The overall nail health is improved by the topical application of the APC compounds. Thus, APC compounds into may be incorporated into nail health enhancing compositions, such as moisturizers, and even into nail polish removers.

In a nail composition, the APC compound is compatible with ingredients such as film-formers, sunscreens, plasticizers, solvents, suspending agents, pigments, and preservatives. A non-exclusive list of film formers includes nitrocellulose, cellulose acetate butyrate, polyurethanes and mixtures of polyurethanes with cellulose acetate butyrate or with nitrocellulose, acrylics, acrylates, polyurethanes, vinyl acrylates, and polyesters.

APC compounds are also compatible with both aqueous and non-aqueous solvents that are used in nail coating compositions. Examples of solvents include methanol, ethanol, propanol, butanol, carbonyl containing solvents such as acetone and butenone, acetates such as ethyl acetate, and chlorinated hydrocarbons such as methylene chloride.

Although the nail compositions of the present invention may be clear, i.e. unpigmented, it is preferred that the nail coating composition includes a pigment component ("nail pigment component"). Non-limiting examples of suitable organic or inorganic pigment components include carmine, bismuth oxychloride, zinc oxide, ferric oxide, ferrous oxide, kaolin, ultramarine violet, ultramarine blue, talc, mica, titanium dioxide, any of the foregoing carried on the surface of talc, mica or titanium dioxide, or mixtures thereof.

Copending U.S. patent applications Ser. Nos. 08/853,271 (now U.S. Pat. No. 5,951,990) and 09/126,191 (now U.S. Pat. No. 5,922,335) disclose that APC compounds are compatible with sunscreens. It is believed that topical sunscreen compositions having both an APC compound and a sunscreen provide synergistic results. The sunscreen may be benzophenone-3 and derivatives thereof, butyl methoxydibenzoylmethane (a non-limiting example of the foregoing is available from Roche Inc. under the tradename "PARSOL-1789") and derivatives thereof, terephthalylidene dicamphor sulfonic acids (a non-limiting example of foregoing is available from L'Oreal under the tradename "MEXORYL SX") and derivatives thereof, titanium dioxide, ethyl methyl cinnamate, ethylhexyl methoxycinnamate, octocrylene and combinations thereof. The derivatives of the foregoing sunscreens may be their inorganic or organic salts.

The combination of sunscreens with APC compounds is expected to be particularly beneficial because APC compounds have been found to inhibit increased production of abnormal elastin (also known as "elastosis"). Since UV radiation is one cause of elastosis, the combination of the APC compound and the sunscreen will provide a superior topical sunscreen composition from the resulting synergism.

Preferably, the topical composition having both a sunscreen and the APC compound will have from about 0.1 wt % to about 20 wt % of at least one APC compound and from about 0.1 wt % to about 25 wt % of at least one sunscreen. The sunscreen is preferably one of the above-disclosed sunscreens. The sunscreen is more preferably a mixture of two or more sunscreens, and most preferably provides both UVA and UVB protection.

The cosmetic cleansing compositions, the moisturizing compositions and the sunscreen compositions of the present invention may additionally have cosmetic additives and adjuvants selected especially from among fats, organic solvents, ionic or nonionic thickening agents, softeners, antioxidants and especially anti-free-radical antioxidants, opacifying agents, stabilizing agents, emollients, silicones, alpha-hydroxy acids, antifoaming agents, hydrating agents, vitamins, fragrances, preservatives, surfactants, fillers, insect repellants, sequestering agents, polymers, propellants, alkylinating or acidifying agents, dyes and colorants, or any other ingredients usually employed in the cosmetics embodiments disclosed above.

The APC compounds may be incorporated into transdermal patches known in the art. The expected advantages of topically administering APC compounds through transdermal patches include localized precise delivery of APC compounds. Precise delivery of APC compounds is particularly desired when the APC compound is used for its skin lightening effects.

The APC compounds may be combined with a number of other ingredients to provide the beneficial effects noted above. For example, the APC compounds may be combined with oxa diacids and/or oxa acids, as noted in co-pending U.S. application Ser. No. 09/126,191, (U.S. Pat. No. 5,922, 335) with alpha-hydroxy acids and/or retinoids. Preferred retinoids are retinol and retinol derivatives. When the APC compound is combined with an oxa diacid, it is preferred that the oxa diacid is 3,6,9-trioxaundecanedioic acid. Other oxa acids and oxa diacids suitable for use in the present invention are disclosed in copending U.S. patent applications Ser. Nos. 08/636,540, 08/850,333, 08/658,089 and 08/863,502, the entire disclosures of which are incorporated herein by reference.

The APC compounds may be combined with sulfites. It has been found that the combination of APC compounds and sulfites in a topical composition uniquely maintains the color of the composition.

The APC compounds may be used as an anti-bacterial system, and as or in a hair conditioner, and as or in a hair shampoo, and as or in an anti-dandruff agent or composition.

One example of a suitable topical composition of the present invention is set forth below as Example 1.

EXAMPLE 1

| Ingredient | Wt % of the Total Composition |
| --- | --- |
| Sodium Ascorbyl/Cholesterol Phosphate | 0.75–6 |
| 3,6,9-Trioxaundecanedioic Acid | 2–12 |
| Ethylhexyl-methoxycinnamate | 2–7.5 |
| Benzophenone-3 | 2–6 |
| Butyl Methoxydibenzoylmethane | 2–3 |
| Tetrasodium EDTA | 0.05–0.25 |
| Glycerin | 2–5 |
| Hydroxyethyl Cellulose | 0.1–1.0 |
| Ammonium Hydroxide 30% | 0.5–4.0 |
| Sorbitan Tristearate | 0.5–3.0 |
| Cetearyl Glucoside | 0.5–4.0 |
| POE (100M) 6000 Monostearate | 0.5–4.0 |
| Methylparaben | 0.1–0.4 |

-continued

| Ingredient | Wt % of the Total Composition |
| --- | --- |
| Sodium Sulfite | 0.05–0.5 |
| Benzyl Alcohol | 0.1–1.0 |
| Cylclomethicone | 1–10 |
| Demineralized Water | qs |

Various modifications and alterations to the present invention may be appreciated based on a review of this disclosure. These changes and additions are intended to be within the scope and spirit of this invention as defined by the following claims.

What is claimed is:

1. A method of cleansing skin and removing cosmetics from skin, the method comprising:

applying to the skin a topical composition comprising a compound in a suitable topical vehicle, said compound being selected from the group consisting of 3'-(L-ascorbyl-2-o-phosphoryl)-cholesterol, 3'-(L-ascorbyl-3-o-phosphoryl)-cholesterol, isomers thereof, salts thereof and mixtures thereof, and removing the topical composition, wherein the compound is present in the composition in an amount effective to cleanse the skin and remove cosmetics from the skin.

2. A method of moisturizing skin comprising:

applying to the skin a topical composition comprising a compound selected from the group consisting of 3'-(L-ascorbyl-2-o-phosphoryl)-cholesterol, 3'-(L-ascorbyl-3-o-phosphoryl)-cholesterol, isomers thereof, salts thereof, and mixtures thereof, wherein the compound is present in the composition in an amount effective to moisturize the skin.

3. A method of improving the appearance of lips comprising:

applying to the lips a topical composition comprising an effective amount of a compound selected from the group consisting of 3'-(L-ascorbyl-2-o-phosphoryl)-cholesterol, 3'-(L-ascorbyl-3-o-phosphoryl)-cholesterol, isomers thereof, salts thereof, and mixtures thereof; and a vehicle, wherein the compound is present in an amount effective to improve the appearance of the lips.

4. The method of claim 3, wherein said topical composition is in the form of a lipstick or a lip balm.

5. The method of claim 3, wherein said topical composition further comprises a pigment.

6. A method of improving the appearance of skin comprising:

applying to the skin a composition comprising:
an iron oxide component; and
a compound selected from the group consisting of 3'-(L-ascorbyl-2-o-phosphoryl)-cholesterol, 3'-(L-ascorbyl-3-o-phosphoryl)-cholesterol, isomers thereof, salts thereof, and mixtures thereof, wherein the composition is applied to the skin in an amount effective to improve the appearance of the skin.

7. A method of enhancing the dispersion on a surface of the human body of a topical composition having a pigment component, the method comprising the step of applying the topical composition on the surface, wherein the topical composition comprises an effective amount of a compound selected from the group consisting of 3'-(L-ascorbyl-2-o-phosphoryl)-cholesterol, 3'-(L-ascorbyl-3-o-phosphoryl)-cholesterol, isomers thereof, salts thereof, and mixtures thereof, and the compound is present in the topical composition in an amount effective to enhance the dispersion of the topical composition on the surface of the human body.

8. A method of enhancing the shine of a nail coating composition comprising:

applying the uncured nail coating composition to a nail; and allowing the nail coating composition to cure, wherein the nail coating composition comprises a compound selected from the group consisting of 3'-(L-ascorbyl-2-o-phosphoryl)-cholesterol, 3'-(L-ascorbyl-3-o-phosphoryl)-cholesterol, isomers thereof, salts thereof, and mixtures thereof, and the compound is present in the nail coating composition in an amount effective to enhance the shine of the nail coating composition.

9. A method of topically administering a composition comprising a compound selected from the group consisting of 3'-(L-ascorbyl-2-o-phosphoryl)-cholesterol, 3'-(L-ascorbyl-3-o-phosphoryl)-cholesterol, isomers thereof, salts thereof, and mixtures thereof, the method comprising:

applying to an area of skin a transdermal patch having said composition incorporated therein.

10. A composition comprising a compound selected from the group consisting of 3'-(L-ascorbyl-2-o-phosphoryl)-cholesterol, 3'-(L-ascorbyl-3-o-phosphoryl)-cholesterol, isomers thereof, salts thereof, and mixtures thereof in a suitable vehicle, wherein the composition is selected from the group consisting of a lip cosmetic, a nail composition, a nail enamel, a make-up remover, and a photoprotective topical composition, and wherein the compound is present in the composition in an amount effective to enhance the performance of the composition, and when the composition is the photoprotective topical composition the compound is present in an amount from about 0.1 wt % to about 20 wt % based upon the total weight of the photoprotective topical composition.

11. The composition of claim 10, wherein the lip cosmetic is a lipstick.

12. The composition of claim 10, wherein the lip cosmetic further comprises an iron oxide component.

13. The composition of claim 12, wherein the nail coating composition is a nail enamel.

14. The composition of claim 10, wherein the pigment additive is a pigment wetter.

15. The composition of claim 10, wherein the pigment additive is a pigment binder.

16. The composition of claim 10, wherein said pigment additive is a pigment disperser.

17. The composition of claim 10, wherein the photoprotective topical composition further comprises a sunscreen selected from the group consisting of benzophenone-3, benzophenone-3 derivatives, butyl methoxydibenzoylmethane, butyl methoxydibenzoylmethane derivatives, terephthalylidene dicamphor sulfonic acids, terephthalylidene dicamphor sulfonic derivatives, titanium dioxide, ethyl methyl cinnamate, ethylhexyl-methoxycinnamate, octocrylene, and mixtures thereof.

18. A topical composition comprising:

a compound selected from the group consisting of 3'-(L-ascorbyl-2-o-phosphoryl)-cholesterol, 3'-(L-ascorbyl-3-o-phosphoryl)-cholesterol, isomers thereof, salts thereof and mixtures thereof;

a second compound selected from the group consisting of an oxa diacid, an oxa acid, and mixtures thereof; and a third compound selected from the group consisting of an alpha-hydroxy acid, a retinoid, and mixtures thereof.

19. The composition of claim 18, wherein the retinoid comprises retinol.

20. The method of claim 1, wherein the topical composition is in the form of a cream, a lotion, an emulsion, a gel, an ointment, a foam, a spray or a mousse.

21. The method of claim 6, wherein the composition comprises from about 0.2 wt % to about 20 wt % of the iron oxide component.

22. The method of claim 6, wherein the composition comprises from about 5 wt % to about 7 wt % of the iron oxide component.

23. The method of claim 12, wherein the nail composition is selected from the group consisting of a nail polish remover, a nail moisturizing composition, and a nail coating composition.

24. The method of claim 12, wherein the nail composition further comprises a second component selected from the group consisting of film-formers, sunscreens, plasticizers, solvents, suspending agents, pigments, preservatives, and mixtures thereof.

25. The composition of claim 10, wherein the composition further comprises a component selected from the group consisting of: antioxidants, alpha-hydroxy acids, vitamins, insect repellents, and any mixture thereof.

* * * * *

UNITED STATES PATENT AND TRADEMARK OFFICE
CERTIFICATE OF CORRECTION

PATENT NO. : 6,162,450
DATED : December 19, 2000
INVENTOR(S) : Ptchelintsev et al.

It is certified that error appears in the above-identified patent and that said Letters Patent is hereby corrected as shown below:

Title page,
Item [54], "Uses of Ascorbyl-Phosphoryl-Cholesterol and Compositions for Practicing Same" should read -- Novel Uses of Ascorbyl-Phosphory-Cholesterol and Compositions for Practicing Same"

Column 9,
Line 48, (line 1of claim 13), "The composition of claim 12" should read -- The composition of claim 23 --.

Signed and Sealed this

Twenty-third Day of October, 2001

Attest:

Attesting Officer

NICHOLAS P. GODICI
*Acting Director of the United States Patent and Trademark Office*